United States Patent [19]
Schoeb et al.

[11] Patent Number: 6,100,618
[45] Date of Patent: *Aug. 8, 2000

[54] ROTARY MACHINE WITH AN ELECTROMAGNETIC ROTARY DRIVE

[75] Inventors: Reto Schoeb, Volketswil; Joerg Hugel, Zurich, both of Switzerland; Niklaus Mendler, Berg, Germany

[73] Assignees: Sulzer Electronics AG, Winterthur, Switzerland; Lust Antriebstechnik GmbH, Lahnau, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/930,649

[22] PCT Filed: Apr. 2, 1996

[86] PCT No.: PCT/CH96/00117

§ 371 Date: Oct. 1, 1997

§ 102(e) Date: Oct. 1, 1997

[87] PCT Pub. No.: WO96/31934

PCT Pub. Date: Oct. 10, 1996

[30] Foreign Application Priority Data

Apr. 3, 1995 [CH] Switzerland ............... 943/95

[51] Int. Cl.[7] .................... H02K 7/09
[52] U.S. Cl. ............ 310/90.5; 310/90; 417/356; 623/3
[58] Field of Search ............ 310/90.5, 90, 198, 310/179, 184; 417/356; 623/3

[56] References Cited

U.S. PATENT DOCUMENTS

| | | |
|---|---|---|
| 4,688,998 | 8/1987 | Olsen et al. ............... 417/356 |
| 4,944,748 | 7/1990 | Bramm ........................ 623/3 |
| 5,055,005 | 10/1991 | Kletschka ............... 417/356 |
| 5,237,229 | 8/1993 | Ohishi ..................... 310/90.5 |
| 5,685,700 | 11/1997 | Izraelev ............... 417/423.7 |
| 5,692,882 | 12/1997 | Bozeman, Jr. et al. ......... 417/45 |
| 5,769,069 | 6/1998 | Caffell ..................... 126/634 |

FOREIGN PATENT DOCUMENTS

| | | |
|---|---|---|
| 0378251 | 7/1990 | European Pat. Off. . |
| 2 681 384 A1 | 8/1992 | France . |
| 2406790 | 8/1975 | Germany . |
| 2457084 | 6/1976 | Germany . |
| 91 08 432 U | 10/1991 | Germany . |
| WO 88/07842 | 10/1988 | WIPO . |

Primary Examiner—Nestor Ramirez
Assistant Examiner—Thanh Lam
Attorney, Agent, or Firm—Townsend and Townsend and Crew LLP

[57] ABSTRACT

The rotary machine comprises a driven rotor and an electric motor having a stator and a driving rotor. The stator is also executed as an electromagnetic bearing for the driving rotor, and the driving rotor of the electric motor together with the driven rotor of the rotary machine forms a rotor unit, i.e. the two rotors form an integral rotor. The rotary machine can for example be a rotary pump, a centrifugal pump, a centrifuge or a stirring apparatus. The rotor can be constructed so as to be easily removable from the stator.

29 Claims, 12 Drawing Sheets

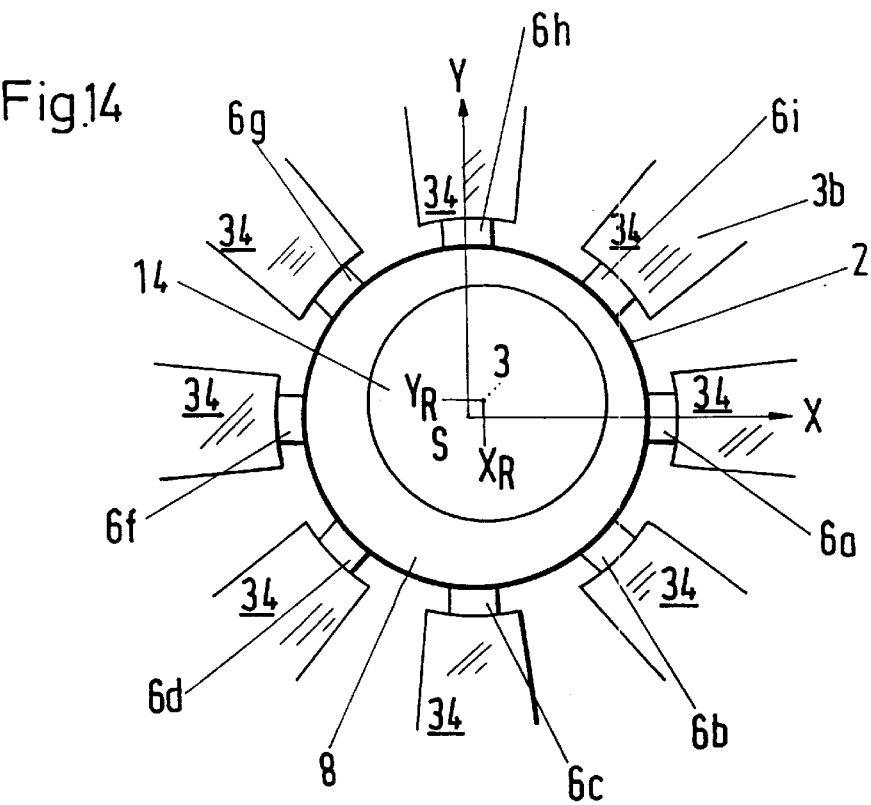
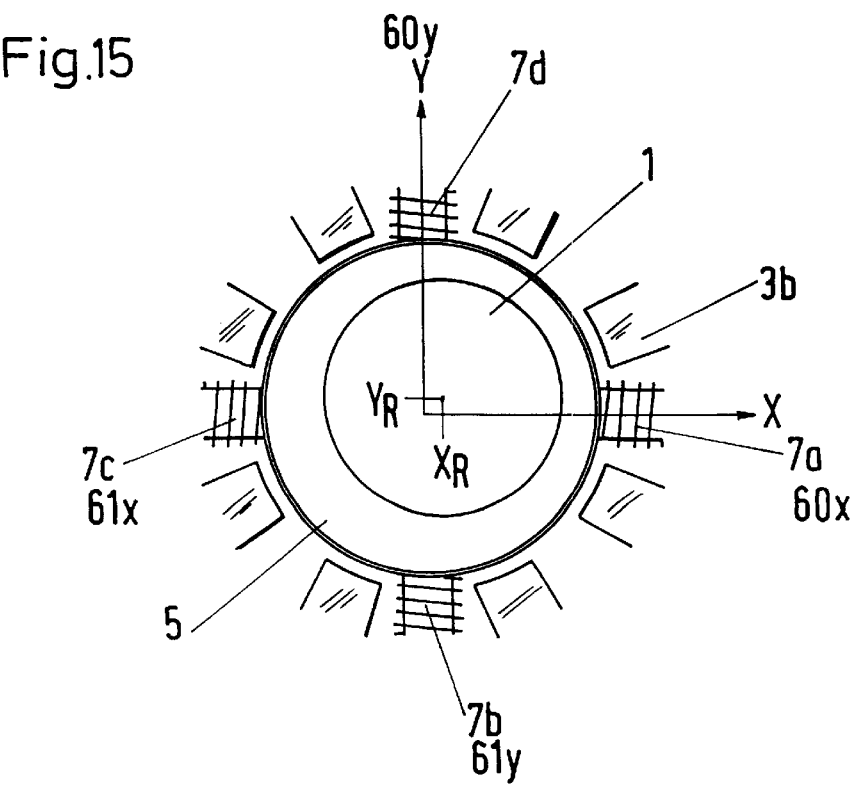

ROTARY MACHINE WITH AN ELECTROMAGNETIC ROTARY DRIVE

BACKGROUND OF THE INVENTION

1. Field of the Invention

The invention relates to an electromagnetic rotary drive including a driven rotor and an electric motor that includes a stator and driving rotor. The invention further relates to pumps and stirring machines driven by rotary drives of this kind.

2. Description of the Prior Art

Rotary pumps with hermetically closed pump housings are used when a complete separation of the fluid to be conveyed from the surroundings is required. Although this requirement would be more easily fulfilled by hose squeezing pumps than by rotary pumps, hose squeezing pumps, so-called peristaltic pumps can frequently not be used because shear forces act on the fluid during their operation by virtue of their specific construction through which the structure of the fluid is impaired. In pharmaceutical and medical fields of application in particular, where mechanically sensitive fluids with long molecular chains or with cells having sensitive cell membranes are to be forwarded, it is necessary to use rotary pumps. In pumping blood, for example, there is the danger that a hemolysis arises as a result of such shear forces, which renders the blood unusable. In contrast to the situation with piston pumps, the fluids are exposed to practically no shear forces in centrifugal pumps so that long molecules with sensitive cells are protected when being conveyed.

A strict material isolation of the fluid to be forwarded can be necessary for two different reasons: on the one hand, an outflow of even the smallest amounts of fluid to the surroundings is to be rendered impossible thereby when contaminating substances are forwarded; on the other hand, an intrusion of foreign substances of any kind into the fluid is to be prevented when the latter must satisfy the highest requirements with respect to purity, which is above all the case when using the pump in the chemical, pharmaceutical or medical fields. Especially for these fields of application, the material isolation of the fluid to be forwarded consists not only in making the intrusion of the surrounding air impossible, but rather particles abraded from relatively moving components of the drive device, of the bearing arrangement or of a sealing arrangement, and lubricants should also be prevented from entering into the fluid.

Pumps of the initially named kind are used during open heart surgery for maintaining the blood circulation, with the fluid to be forwarded being the blood of the patient. It is self evident that in such cases the highest demands are made with respect to maintaining the purity of the fluid to be pumped.

When using conventional drive devices, bearing devices and sliding ring seals, it proved impossible to seal off the pump housing completely relative to the surroundings and at the same time to prevent the production of abraded particles from relatively moved components and the intrusion of such abrasion particles and of lubricants into the fluid.

By means of the magnetic bearings known for a longer period of time, it was possible to replace conventional roller or sliding bearings by a bearing apparatus which enables not only contact-free journalling, for example in the form of a buoyant sliding bearing, but also enables lubricant-free journalling.

A further advance in the same direction is the development of three phase current motors with a separation of the stator from the rotor, so-called split tube motors.

For example, EP-0 551 435 describes an electromagnetic rotary drive for a rotary pump with a hermetically sealed pump housing and a pump rotor which is journalled by means of a contact-free bearing device and is driven by a split tube motor.

This electromagnetic rotary drive for the pump is constructed in a complicated and expensive manner and is relatively voluminous, with its axial dimension in particular being large. The magnetic bearings require a large amount of space.

SUMMARY OF THE INVENTION

The object of the present invention is to provide an improved, compact and simple electromagnetic rotary drive for rotary pumps, mixers, stirring mechanisms and other devices.

This object is satisfied in accordance with the present invention by an electromagnetic rotary drive having an electric motor with a stator for bearing and driving an integral rotor.

In the electromagnetic rotary drive in accordance with the invention for devices such as rotary pumps etc., the bearing device and the drive device form a combined, contact-free and lubricant-free bearing/drive device in accordance with the principle of the so-called bearing-free motor, the combined bearing/drive rotor of which is executed in such a manner that it also takes over the function of the rotor of the apparatus, such as for example a pump rotor, mixer rotor or stirrer rotor, in addition to the function of the rotor of the electric motor. Rotors of this kind are called integral rotors.

The principle of the 'bearing-free' motor resides in the fact that, on the one hand, the rotor of a rotary field machine and a journalled shaft arrangement result in the combined bearing/drive rotor and in the fact that, on the other hand, the stator of the rotary field machine and the non-rotating part of a bearing arrangement produce a bearing/drive stator. In the arrangement of a 'bearing-free motor' as bearing/drive arrangement of a rotary pump, the pump housing and the bearing/drive stator are of fixed location in operation, while the bearing/drive rotor as well as the pump rotor would be two rotatable components, which together form the integral rotor in accordance with the invention.

In accordance with the invention the rotary field motor contains a drive winding with the number of pole pairs p and a control winding with the number of pole pairs p+1 or p−1; the rotation of the integral rotor about its axis of rotation is actively controlled or regulated via the drive winding, and the position of the integral rotor in the plane extending perpendicular to the axis of rotation is actively controlled via the control winding. The position of the integral rotor in the direction of the axis of rotation and its tilting with respect to the named plane are passively stabilized by reluctance forces.

With the construction in accordance with the invention, which represents a special form of the 'bearing-free motor' for a rotary pump through the provision of the integral rotor, it becomes possible to build extremely compact rotary pumps.

During the use of such an electromagnetic rotary drive, e.g. a rotary pump for forwarding fluids which are extremely susceptible to contamination, such as, for example, blood during open heart surgery, it is necessary after use to perfectly clean all parts which come into contact with the blood and/or to remove all traces of blood from these parts before the rotary pump is used for a further operation. The reason for this is that it must under all circumstances be avoided that the blood of a first patient enters into the circulatory system of further patients, since foreign blood can, in general, lead to undesirable, and even life threatening, reactions. Since an unobjectionable cleaning of the pump is not possible, there is no other possibility of preventing all dangers to the patient than to replace the rotary pump or at least the parts of the rotary pump which come into contact with the blood after every use. This means that the financial outlays for the rotary pump alone are considerable, given the large number of such operations. Through the use of the rotary pump in accordance with the invention with the new integral rotor, considerable costs can be saved with a suitable constructional design in that one chooses a mode of construction in which the pump housing with the integral rotor accommodated therein are freely accessible from the outside and are easily removable. Only these two parts come into contact with and are contaminated by the fluid to be forwarded and hence need be replaced after each operation. They are thus constructed as disposable units, whereas the remaining components need not be replaced, but can be used for a large number of operations.

The integral rotor, which consists of the electromagnetically active components of the bearing/drive rotor, and of the rotor of the device driven, i.e. effectively the pump rotor, is preferably executed in such a manner that it has a ring-shaped rotor disc in which the named electromagnetically active components are accommodated and to which rotor blades are fastened.

The said electromagnetically active components of the rotor disc of the integral rotor comprise magnets such as ring magnets, disk magnets or shell magnets as well as iron such as iron yokes or iron crosses and windings, depending on the type of rotary field motor selected. They can be embedded in parts of the rotor disc welded to one another or molded onto the rotor disc by means of an injection molding composition and can be completely enveloped by the injected material.

In order that the integral rotor and the rotor housing, which are constructed in certain cases as disposable units as mentioned, can be manufactured economically, it is advantageous to design them in such a manner that all parts which come into contact with the fluid consist of plastic. Otherwise, expensive materials must be used, since, on the one hand, it must be seen to in selecting the materials that no chemical reactions take place between the material and the fluid, and, on the other hand, a disturbance of the electromagnetic fields required for the drive and the control must be avoided.

The pump housing can have, in addition to the said axial inlet, a further inlet for the fluid lying opposite to the first. The influence that a corresponding design has with respect to the pressure relationships and the measures required for controlling the position of the integral rotor will be discussed later.

Accordingly, it is possible to construct the pump housing in such a manner that, in addition to the said at least approximately radial outlet, it has a further outlet which is arranged to be centrally symmetric with respect to the first outlet. The influences on the pressure relationships and the measures required for controlling the position of the integral rotor which arise therefrom will also be discussed later.

The rotary pump in accordance with the invention can be executed as an axial pump, with the rotor blades being formed by the vanes of a vaned wheel which is preferably fastened to the inner edge of the rotor disc of the integral rotor. A centrifugal pump is mainly used, however, since it enables the generation of a high pressure. The principle of the combined journalling and drive of an apparatus such as, for example, a pump rotor can also be transferred to all other types of centrifugal pumps such as side channel pumps, peripheral pumps, Tesla pumps or fluid ring pumps, to mixing apparatuses or to other apparatuses which are to be driven in rotation.

In a simple type of a centrifugal pump, rotor blades are merely provided on one surface of the ring-like rotor disc of the integral rotor.

It is however also possible to arrange rotor blades on both surfaces of the integral rotor or to integrate the rotor blades in a rotor.

The bearing/drive rotor can be executed as a conventional rotary current stator of axially short design with a drive winding having a number of poles p and a control winding with a number of poles p+1 or p−1. A stator design of this kind has considerable disadvantages since in such a design only a small part of the winding is located in the groove as a result of the short length of the stator in comparison with its diameter. A stator constructed in this manner not only has a large winding head scatter, but the efficiency is also poor. In addition, it will be difficult, for example in a centrifugal pump, to guide the connection stub through between the winding heads.

The bearing/drive stator is generally executed in such a manner that it has a plurality of elongate coil cores arranged about the integral rotor with a common magnetic yoke, with each coil core receiving a partial winding for each winding string of the drive winding with the number of pole pairs p and a partial winding for each winding string of the winding string of the control winding having the number of pole pairs p+1 or p−1. A sinusoidal geometrical distribution of the drive flux and of the control flux is approximated by the ratio of the numbers of turns of the partial windings of a winding string. In this way, a design is achieved which makes do with very short winding heads. It is possible that at least one of the partial windings has the winding number zero.

In a usual embodiment, the above mentioned coil cores are arranged radially with respect to the axis of rotation of the integral rotor. The coil cores and the iron yoke can form a unit in this case. This unit can, for example, be made as a stack of individual sheet metal plates with long grooves.

In a further preferred exemplary embodiment, the coil cores have the shape of an "L", with the one limb of the "L" being arranged parallel to the axis of rotation of the integral rotor and the other limbs of the "L" being directed radially inwards towards this axis of rotation in order to conduct the flux radially to the integral rotor. A rotary field motor with a rotor geometry of this kind can be designated as a temple motor. The temple motor is particularly suitable for accommodating a replaceable arrangement of a pump housing and integral rotor conceived as a disposable unit.

The drive part of the bearing/drive arrangement can be executed in accordance with the principle of a synchronous motor or an induction motor. The synchronous motor generally leads to constructions with higher efficiency and above all lower rotor losses. In particular, a construction in accordance with the principle of the reluctance motor or of the synchronous motor excited by permanent magnets can be chosen for this synchronous motor.

A corresponding apparatus can be provided as a part of the control or regulatory device of the new rotary pump in order to determine the drive flux angle which is required for the control of the drive of the bearing-free motor.

This apparatus can, for example, contain one or more flux sensors. The new rotary pump can further contain a detector device for determining the position of the integral rotor as a part of its control or regulatory system. A detector device of this kind generally has an X-Y detector by means of which the position of the integral rotor can be determined in a plane perpendicular to the axis of rotation. The X-Y detector can contain one or more flux sensors.

A preferred X-Y detector has a plurality of symmetrically distributed flux sensors in order to measure the partial fluxes at discrete positions. In addition to the drive flux angle, the X component and the Y component of the position of the integral rotor are determined from the partial fluxes through the angle of rotation of the rotary field motor. This is done by a weighted summation of the partial fluxes over, in each case, half the perimeter in the positive and negative X direction as well as in the positive and negative Y direction, by taking the absolute value of the sum obtained and subsequently the difference formation of the components in the positive and negative X direction as well as of the components in the positive and negative Y direction.

The flux sensors used for the regulation of the drive and/or for the regulation of the position of the integral rotor in the X-Y plane can, for example, be arranged in the air gap between the pump housing and the bearing/drive stator.

It is also possible to provide the flux sensors in the core of the elongate coils. The flux sensors can, for example, be Hall elements of magnetoresistive flux sensors. The fastening of the flux sensors can be performed at one tooth of the stator of the rotary field motor, for example, by adhesive bonding. A further possibility for fastening the flux sensors consists in embedding them in recesses in the stator.

The X-Y detector can also be designed in such a manner that it contains an eddy current detector in order to measure the distance in the X-Y plane extending perpendicular to the axis of rotation of the integral rotor from a conducting layer present in the integral rotor. This conducting layer can be formed, for example, of a metallic ring or of a thin metallic layer or of the rotor magnet itself if the latter is made of a conducting material such as NdFe. Instead of a single eddy current detector, two eddy current detectors lying opposite one another in the X and Y direction can also be provided which produce detector signals. In this way, the X and Y components of the position of the integral rotor in the X-Y plane extending perpendicular to the axis of rotation can be determined.

The X-Y detector can also be executed in such a manner that it contains sensor windings which are arranged in the stator of the rotary field motor in addition to the drive winding and the control winding in order to determine the position of the integral rotor in the X-Y plane extending perpendicular to its axis of rotation by means of evaluation of the electrical impedance of these sensor windings.

A further possibility of designing the X-Y detector consists of providing an optical device by means of which the position of the integral rotor in the X-Y plane extending perpendicular to its axis of rotation can be measured with the help of light whose wavelength lies in the optical window of the fluid.

The said detector device can also have a Z detector in addition to the X-Y detector, different variants of which have been described in detail, in order to measure the axial position of the integral rotor and to emit a corresponding Z position signal.

In this case, the Z position signal determined can form the actual value for the determination of a control signal for a technical control stabilization of the axial position of the integral rotor. For such a technical control stabilization of the axial position of the integral rotor, a magnetizing current can also be set up with a current component in the direction of the drive flux of the bearing/drive sector.

The new rotary pump preferably has a pressure determining device by means of which the pump pressure can be determined from the Z position signal or from the control signal derived therefrom.

In general, the new rotary pump is also equipped with a through-flow or flow rate determining device which determines the temporal through-flow of the fluid from the Z position signal as well as from the speed of rotation of the integral rotor and from the torque-forming component of the drive current.

BRIEF DESCRIPTION OF THE DRAWINGS

FIG. 14 is the bearing/drive stator with the integral rotor of FIG. 11 in the same representation as in FIG. 11, however with a different position of the integral rotor and with a flux sensor for positioning the rotor;

FIG. 15 is a further bearing/drive stator with an integral rotor in a highly simplified representation, seen from above, with a possible arrangement of the eddy-current distance sensors being shown;

DESCRIPTION OF THE PREFERRED EMBODIMENTS

Figure 1:
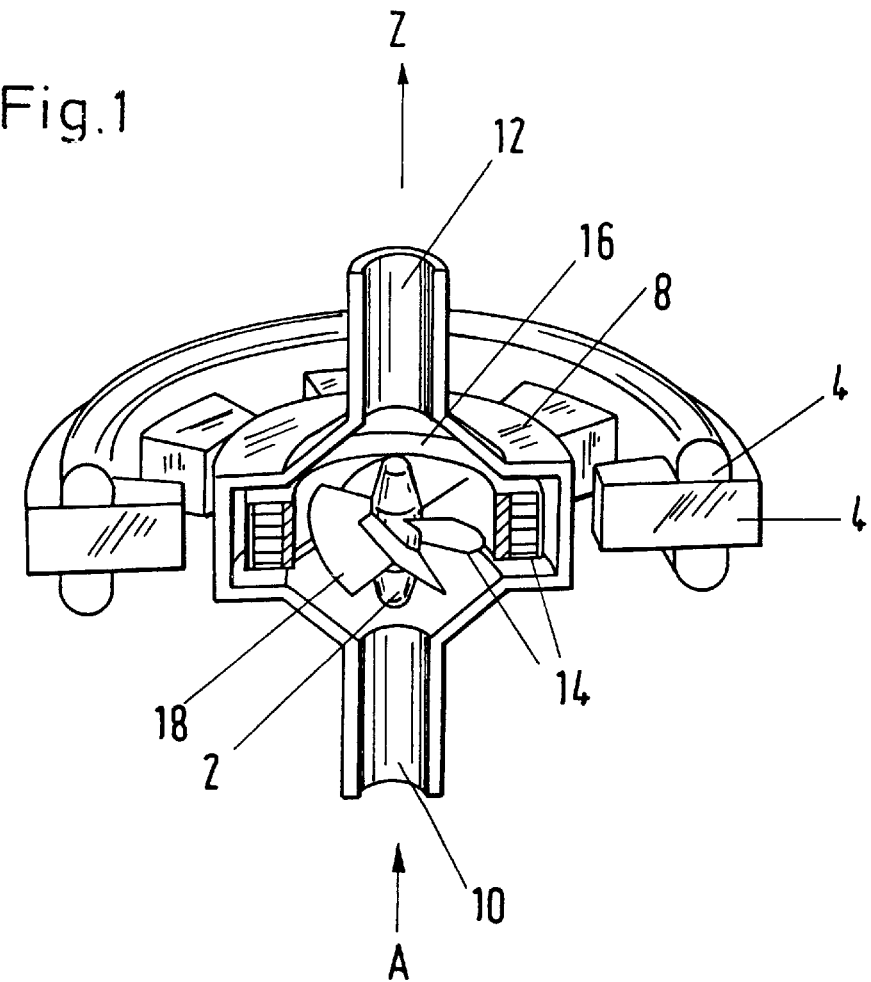
FIG. 1 is a rotary pump in accordance with the invention in a schematic sectional representation through the axis of rotation.

The rotary pump 2 shown in FIG. 1 with the axis of rotation 3 has a bearing/drive stator 4 of a bearing/drive arrangement operating in accordance with the principle of the 'bearing-less motor'. The bearing-less motor operates in accordance with the principle of the rotary field motor. The bearing/drive stator 4 contains electromagnetically active components 6 which will be described in detail later. A pump housing 8 with an axial inlet 10 and a radial outlet 12 for a fluid to be forwarded is arranged in the bearing/drive stator 4. The inlet 10 and the outlet 12 serve to connect the rotary pump 2 to a non-illustrated line network. A first arrow A indicates the inflow direction, a second arrow Z indicates the outflow direction of the fluid. The bearing/drive stator 4 and the pump housing 8 are components of the rotary pump 2 which are spatially fixed or non-rotating during operation. Located in the interior of the pump housing 8, there is an integral rotor 14 which is formed by a rotor disc 16 and rotor blades 18 connected thereto, with non-illustrated electromagnetically active components of the rotary field motor being accommodated in the rotor disc 16. The integral rotor 14 serves at the same time as a bearing/drive rotor and as a pump rotor and is thus the only rotatable component of the rotary pump 2.

Figure 2:
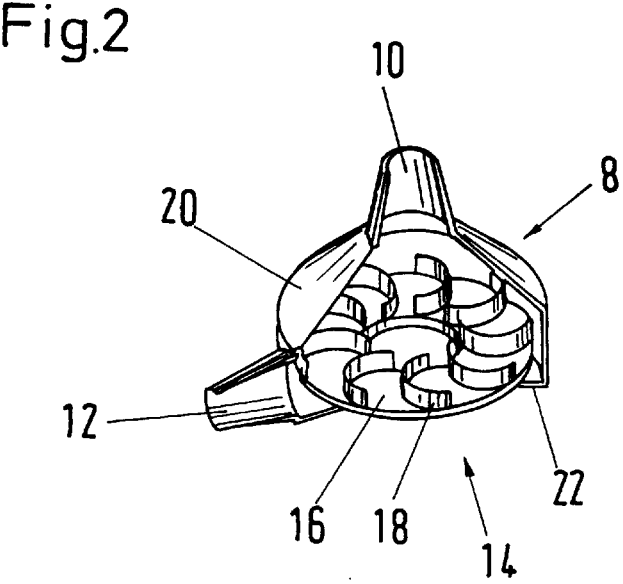
FIG. 2 is a pump housing with an integral rotor in a first embodiment in a perspective view.

The pump housing 8 illustrated in FIG. 2 comprises an axial inlet 10 and a radial outlet 12, a conical upper wall 20 and a substantially planar lower wall 22. The integral rotor 14 is visible in the pump housing 8, here with a rotor disc 16 executed to be ring-shaped and the rotor blades 18 which are fastened to the upper surfaces of the rotor disc 16. An integral rotor of this kind is used in a rotary pump executed as a centrifugal pump.

It was mentioned at the outset that the number and therefore the constructional arrangement of the inlets and outlets influence the pressure relationships and thus the position of the integral rotor in the pump housing. In order to minimize this influence in the X-Y plane, it is advantageous when executing the rotary pump as a centrifugal pump to provide two such outlets lying opposite to one another. In this connection, it would even be advantageous to provide a plurality of outlets, which, however, would greatly complicate the construction.

Figure 3:
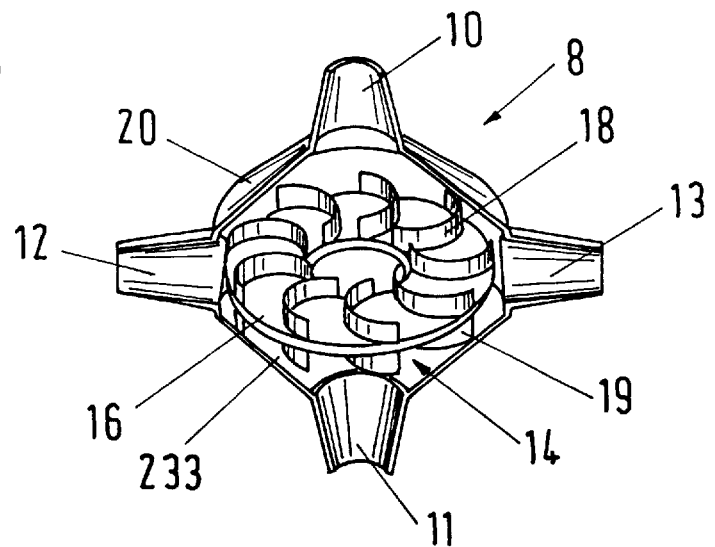
FIG. 3 is a pump housing with an integral rotor in a second embodiment in a perspective view.

The pump housing 8 shown in FIG. 3 has a further axial inlet 11 and a further radial outlet 13, with both the inlets 10, 11 as well as the outlets 12, 13 lying opposite to one another respectively. The pump housing 8 therefore also has a lower conical wall 233 in addition to the upper conical wall 20, and the rotor disc 16 of the integral rotor 14 is equipped with rotor blades 18 and 19 on its upper and lower surfaces respectively.

Figure 4:
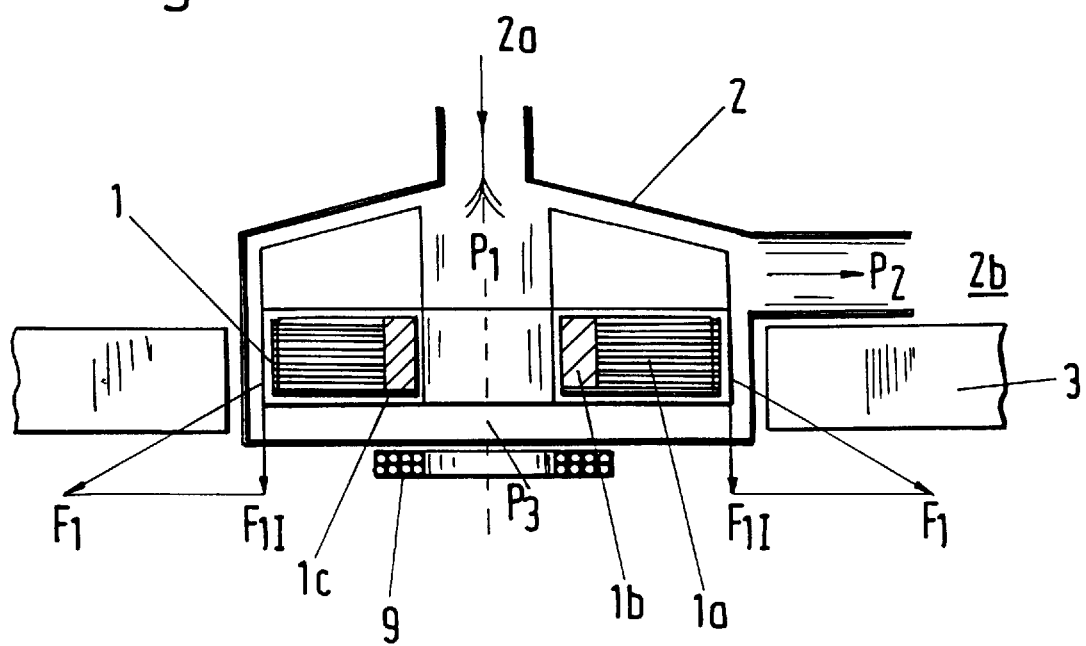
FIG. 4 is a rotary pump with an additional axial position sensor in a highly simplified representation, in a section along the axis of rotation.
Figure 5:
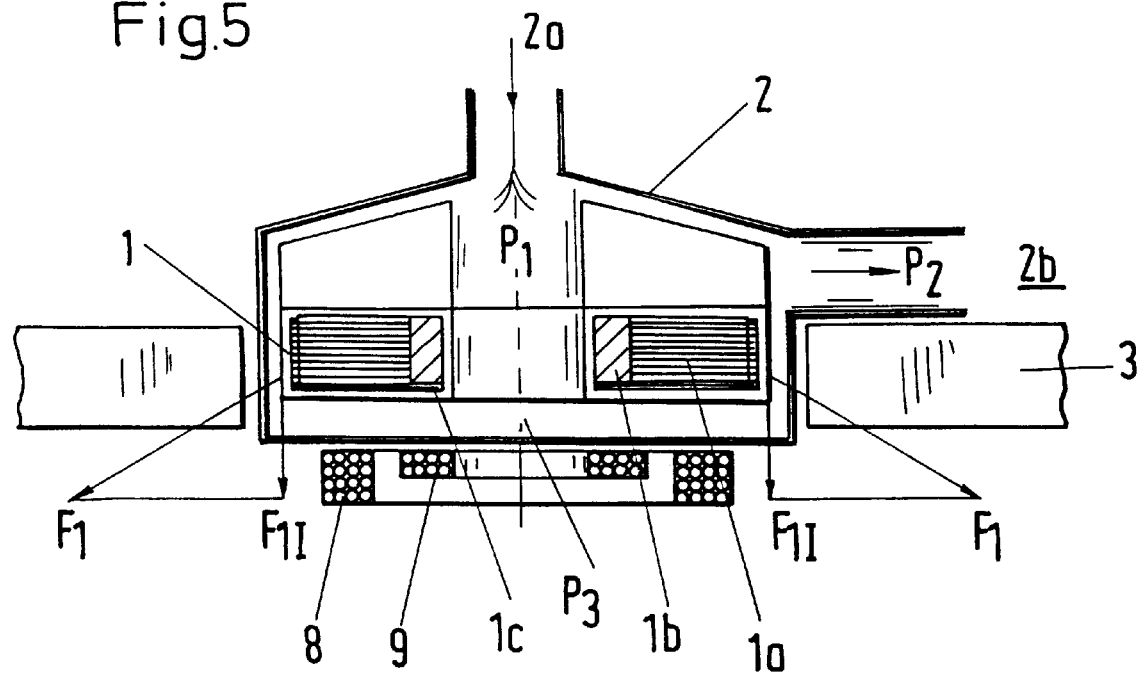
FIG. 5 is a further rotary pump with an additional axial position sensor and an additional axial winding in the same representation as FIG. 3, in a simplified portrayal in a section along the axis of rotation.

In a design of the rotary pump as an axial pump as well as a centrifugal pump with only one axial inlet, an axial force acts on the integral rotor as a result of the pressure gradient in the axial direction. FIG. 4 and FIG. 5 show, for the example of a centrifugal pump, how this axial force can be compensated in that one or more additional axial windings 8, 9 are provided.

Figure 6:
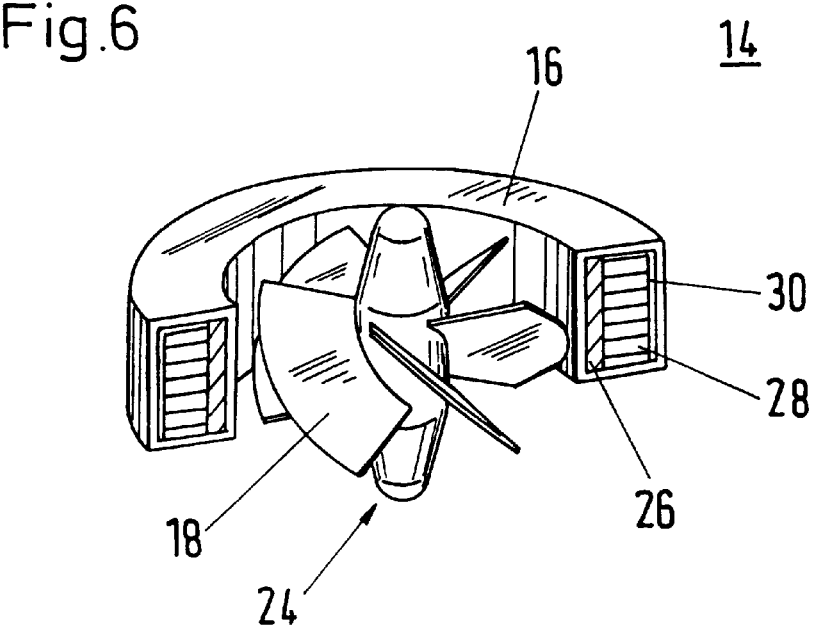
FIG. 6 is an integral rotor for an axial pump in a perspective view.

The integral rotor 14 of FIG. 6 is intended for a rotary pump operating in accordance with the principle of an axial pump. It consists substantially of the ring-shaped rotor disc 16 and a vaned wheel 24 arranged in the central free space of this rotor disc 16 with its vanes forming the rotor blades 18. The rotor disc 16 illustrated in a cut-away view contains electromagnetically active components in its interior for a bearing/drive arrangement with a rotary field motor operating as a synchronous motor, namely a rotor-side yoke iron 26, a magnet 28 and a conductive layer 30; this layer 30 can consist of a metal ring or of a thin metal layer. If the magnet 28 is constructed of a conducting material, it can itself be used as the conductive layer. It is used as the measurement unit for the measurement of the radial rotor position by means of eddy current distance sensors.

FIG. 7 again shows the integral rotor 14 of FIG. 3 which can be used in a centrifugal pump or a side channel pump, with upper rotor blades 18 and the lower rotor blades 19 as well as with the rotor disc 16 shown cut away in which the rotor-side yoke iron 26, the magnet 28 and the conducting layer 30 which are to be considered as the rotating parts of a synchronous motor, are enclosed.

Figure 8:
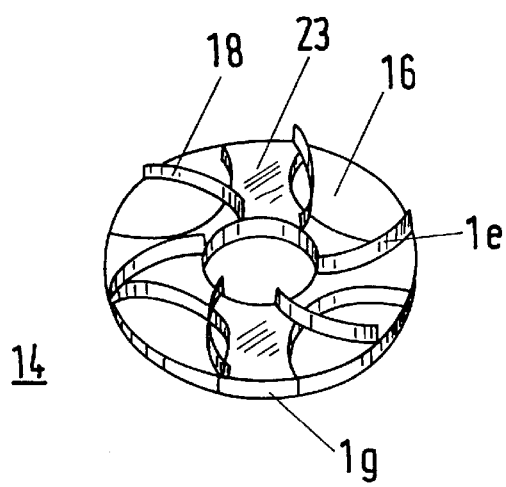
FIG. 8 is an integral rotor for a centrifugal pump for use with a drive device operating in accordance with the principle of a reluctance motor, in a perspective view.

The integral rotor 14 shown in FIG. 8 with the ring-shaped rotor disc 16 is intended for a rotary pump conceived as a centrifugal pump whose bearing/drive arrangement has a rotary field motor which operates in accordance with the principle of a reluctance motor. Only the upper surface of the rotor disc 16 is equipped with the rotor blades 18. An iron cross 23 is embedded in the rotor disc as is usual for reluctance motors.

Figure 9:
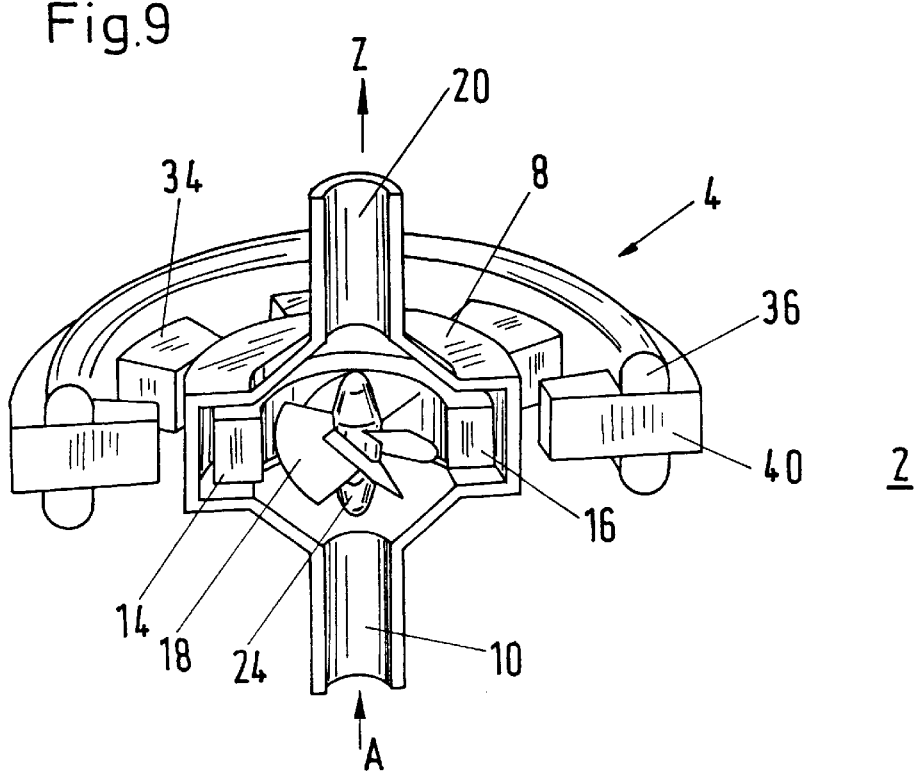
FIG. 9 is a rotary pump executed as an axial pump in a simplified representation, in a perspective view.

FIG. 9 shows more clearly the rotary pump 2 executed as an axial pump. The cut away pump housing 8 has the axial inlet 10 and the axial outlet 12, with arrows A and Z showing the direction of forwarding of the fluid. Located in the pump housing 8 is the integral rotor 14 which, as described earlier, is formed by the rotor disc 16 and the vaned wheel 24 with its vanes acting as rotor blades 18. Furthermore, the bearing/drive stator 4 is visible in FIG. 9. It consists of the laminated metal stator pack with grooves, teeth and a yoke iron as well as a winding inserted into the stator grooves, the winding consisting of a partial winding with the pole number p and a partial winding with the pole number n+1 or n−1.

It has a plurality of radially oriented rod-like coil cores 34 which are arranged about the pump housing 8, windings 36 and a stator-side yoke iron 38 which are the spatially fixed, electrically active components 6 of the bearing/drive arrangement of the rotary pump 2.

Figure 10:
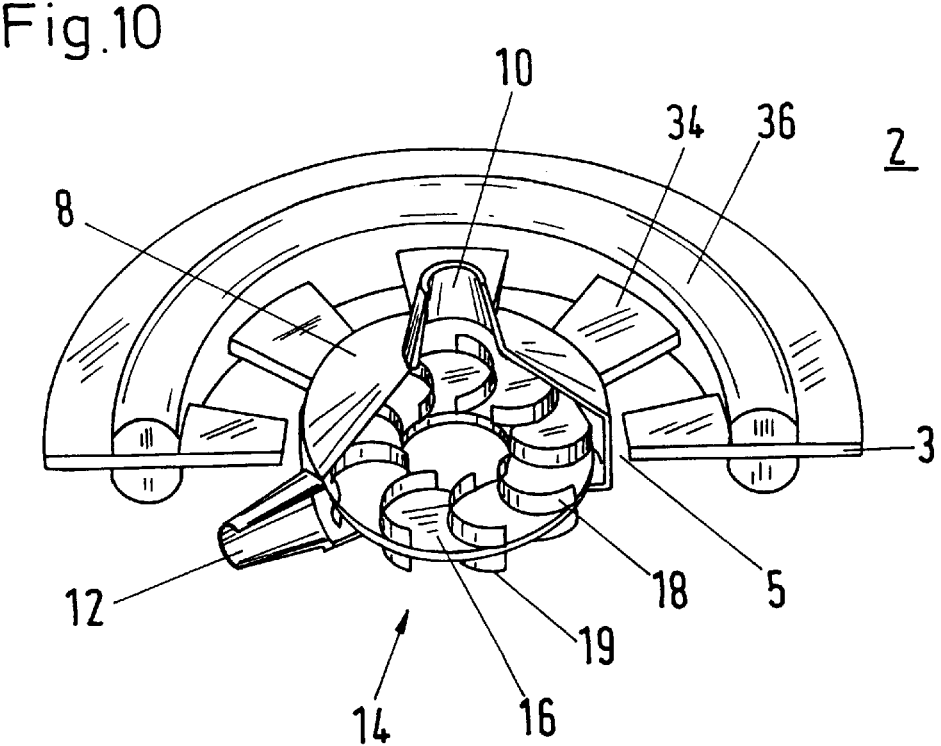
FIG. 10 is a rotary pump executed as a centrifugal pump in a simplified representation, in a perspective view.

An embodiment is shown in FIG. 10 in which the rotary pump 2 is executed as a centrifugal pump. One can see the pump housing 8 with the axial inlet 10 and the radial outlet 12 as well as the integral rotor 14 with the ring-shaped rotor disc 16 and the rotor blades 18. Furthermore, the radially directed coil cores 34, the windings 36 and the rotor-side yoke iron 38 are illustrated in a simplified manner.

Figure 11:
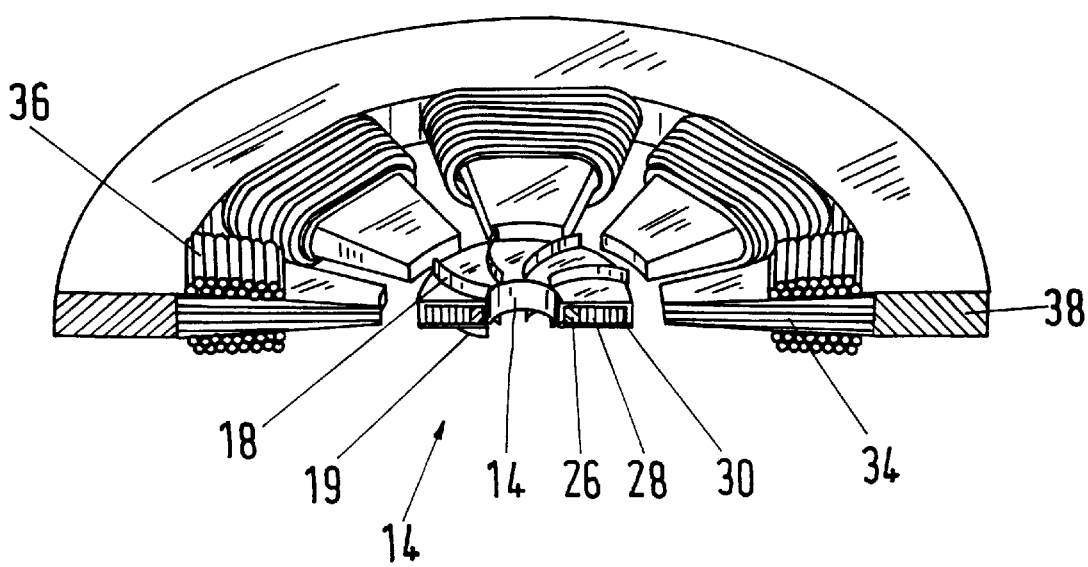
FIG. 11 is a bearing/drive stator with an integral rotor, with the pump housing being omitted for the sake of simplicity, in a perspective view.

FIG. 11 shows more clearly the electromagnetically active components on the rotor side and the stator side. In this illustration, the pump housing was left out as an electromagnetically inactive component. Located at the center is the cut away integral rotor 14 with the rotor disc 16, which is provided with the rotor blades 18, 19. Embedded in the rotor disc 16, as described above, are the yoke 26, the magnet 28 and the conducting layer 30. The integral rotor 14 is surrounded by the likewise cut away bearing/drive stator, which has the coil cores 34, the windings 36 and the rotor-side yoke 38.

Figure 7:
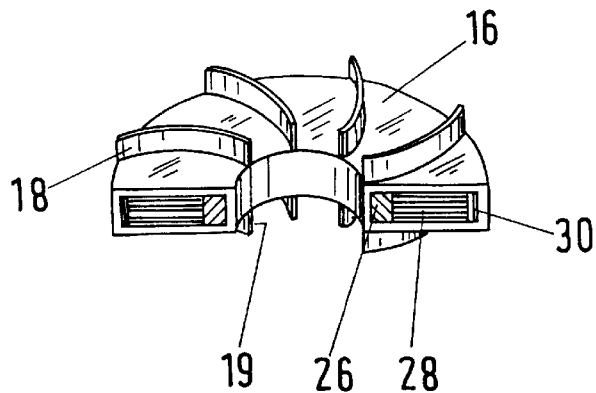
FIG. 7 is an integral rotor for a centrifugal pump in a perspective view.
Figure 12:
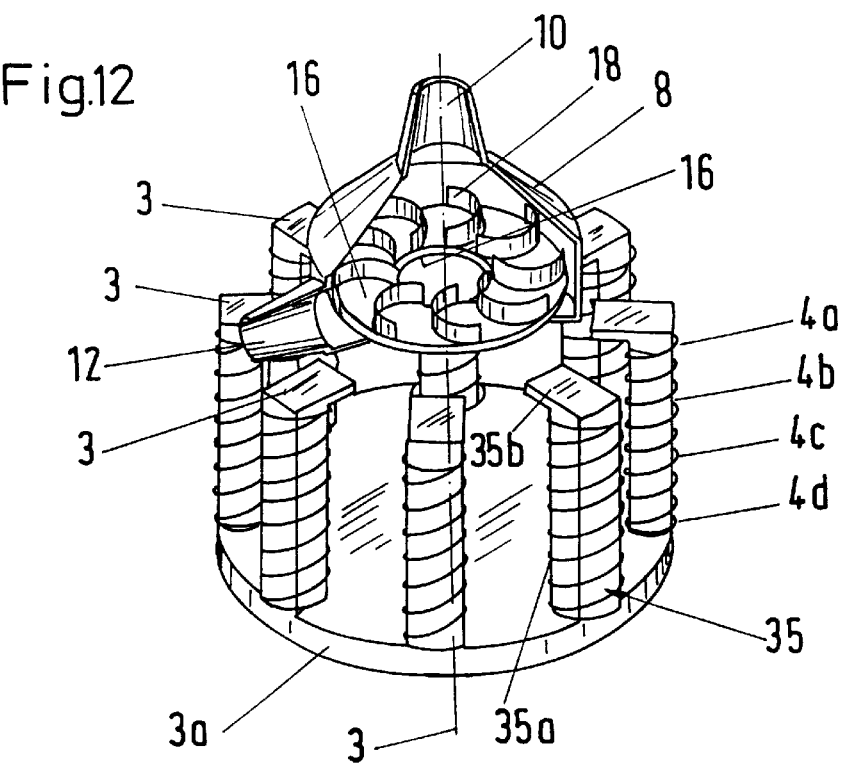
FIG. 12 is a rotary pump with a bearing/drive arrangement executed as a temple motor in a perspective view.

In FIG. 12 the rotary pump 2 is illustrated with a bearing/drive arrangement whose rotary field motor is a so-called temple motor. For the sake of clarity of this figure, the pump housing 8 is not shown in its assembled position but above it. As has already been described a number of times, the pump housing 8 has an axial inlet 10 and a radial outlet 12. It contains an integral rotor 14 with the ring-shaped rotor disc 16, on whose upper surface the rotor blades are visible. Instead of the radially extending coil cores 34 as shown in FIGS. 7, 8 and 9, the temple motor has symmetrically distributed coil cores 35 each of which has the shape of an 'L', with the long limb 35a of the 'L' extending vertically or parallel to the axis of rotation 3, whereas the short limb 35b of the 'L' is directed radially inwards towards the axis of rotation 3. The temple motor therefore does not differ in its electrical manner of operating from the rotary field motor shown in FIG. 11, but it permits the pump housing 8 to be arranged practically in the bearing/drive stator in such a manner that it can be sunken and thus in a space saving manner in the assembled state, but can nevertheless be removed in a simple manner. Furthermore, the windings 36 as well as the yoke 38 are visible.

The above description relates substantially to the constructional design of the rotary pump with its bearing/drive arrangement and to the control system. In the following, possible measures for the technical control design of the rotary pump are presented.

In order to determine the required drive flux angle for the drive regulation of the bearing-free motor, at least one flux sensor can be provided. The drive flux angle can then be determined via the partial flux component. The speed of rotation of the motor can be likewise determined via the same arrangement. The arrangement and the execution of the flux sensors will be described later.

For the technical control stabilization of the position of the integral rotor, its momentary position, or its deviation from the desired position, must be determined. A detector apparatus is provided for this purpose which has an X-Y detector and also a Z detector. The X-Y detector serves for the determination of the position of the integral rotor in the X-Y plane extending perpendicular to the rotor axis, and the Z detector serves for the determination of the position of the integral rotor along the axis of rotation of the integral rotor.

The X-Y detector can have a plurality of flux sensors in a first embodiment and they can also be used for the regulation of the drive. In this case, the flux sensors can be Hall elements or magnetoresistive flux sensors mounted, for example, on one tooth of the stator, possibly by adhesive bonding, or embedded in a groove of the stator.

Figure 13:
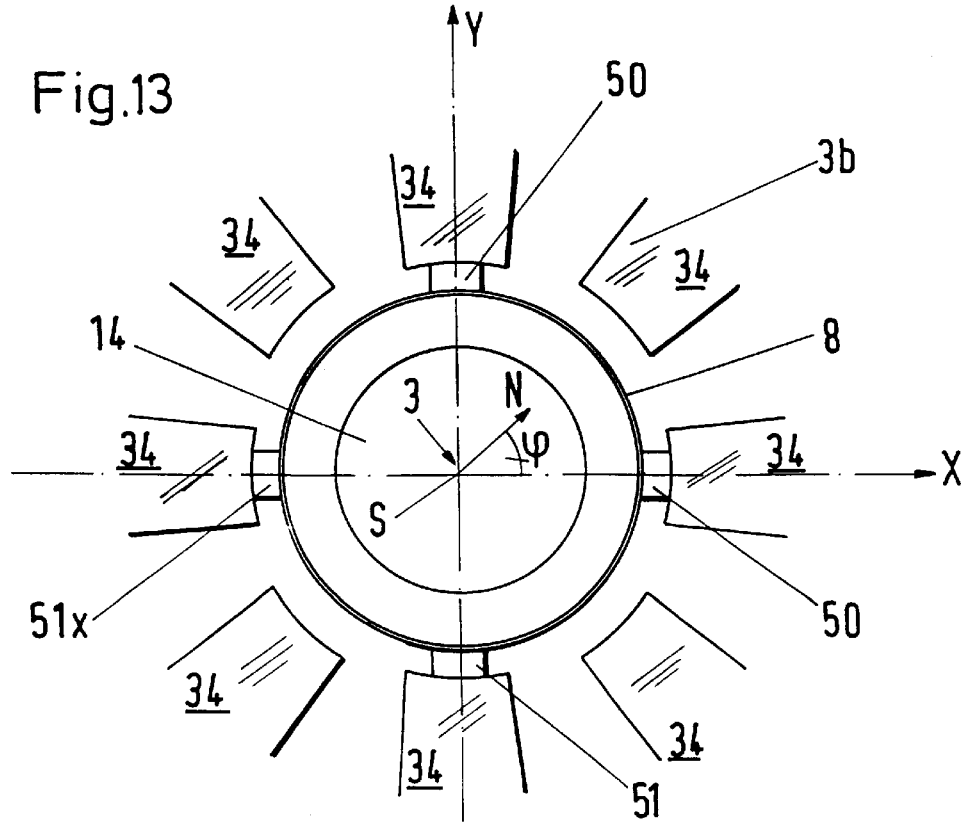
FIG. 13 is a bearing/drive stator with an integral rotor in a highly simplified representation, in a first operating state, seen from above and with a flux sensor for measuring the angle.

FIG. 13 shows the contour of the pump housing 8 and the integral rotor 14 located therein, which takes on its correct, centered position. The axis of rotation 3, visible as a dot, forms the point of intersection of an axis crossing with the X and Y axes. The pump housing 8 is surrounded by the coil cores 34 or stator teeth. A plurality of flux sensors 50x, 50y, 51x, 51y is arranged in the air gap between the rotor housing 8 and the coil cores 34 or the stator arms, and are the detector part of a detector system for the determination of the direction of magnetization (angle alpha of the integral rotor 14 in the X-Y plane defined by the axes X and Y extending perpendicular to the axis of rotation 3); this position will be designated as the angular position of the integral rotor 34 for short. The influence of a displacement of the rotor away from the center on the determination of the angular position of the integral rotor can be compensated by the arrangement of two flux sensors lying opposite to one another in each case.

A similar arrangement is illustrated in FIG. 14 with the pump housing 8 and the integral rotor 14 located therein, which does not take on its correct, centered position here but—measured along the axes X and Y—is displaced by x and y from this position so that its axis of rotation does not coincide with the point of intersection of the X and Y axes. In this arrangement, eight flux sensors 50a to 50h are located in the air gap between the rotor housing 8 and each of the eight coils 34, which are likewise shown.

The flux sensors serve here not only for the determination of the angular position of the integral rotor, but at the same time for the determination of its X-Y position. This is done through a weighted summation of the partial fluxes measured with the help of the flux sensors over half the periphery in the X direction and half the periphery in the Y direction and in the opposite direction in each case, by forming the absolute value and by subsequent difference formation (of the component in the X direction and in the opposite direction as well as of the component in the Y direction and in the opposite direction).

The X-Y detector can also be made as an eddy current distance sensor in a different type of design. The distance to the conducting layer in the rotor disc of the integral rotor, which has been mentioned a number of times, is measured by an eddy current distance sensor of this kind.

In a different embodiment in accordance with FIG. 15 the X-Y detector contains sensor windings 60x, 60y, 61x, 61y. The remaining elements shown in FIG. 15, correspond to those of FIG. 12. The sensor windings determine the X-Y position of the integral rotor 14 through an evaluation of their electrical impedance.

Figure 16:
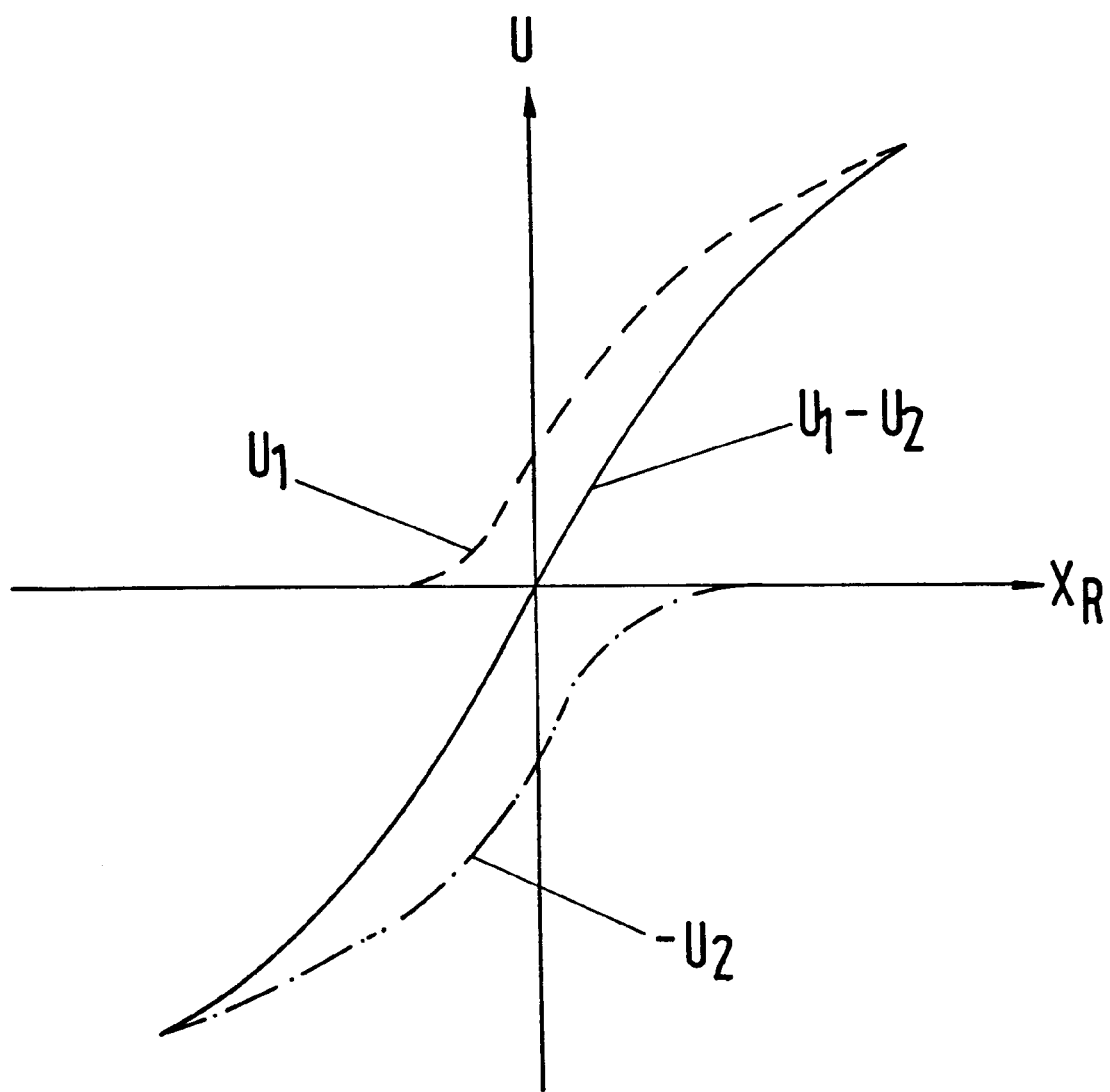
FIG. 16 is a diagram for obtaining a linear position signal ($U_1-U_2$) through taking the difference of the signals $U_1$ and $U_2$ with respect to the position sensors. Illustration of the control flux in dependence on the position of the integral rotor in the X direction.

FIG. 16 shows the relationship between the voltage U and the deviation x of the integral rotor from its desired position in the direction of the X axis. It can be seen from this that the relationship U/x is linear in the desired manner in the central region, which is decisive for the control system, provided the sensor signal is derived from the difference of two oppositely disposed sensors with restricted, linear measurement ranges.

A further embodiment for the design of an X-Y detector consists in using an optical device in which light whose wavelength lies in the range of the optical window of the forwarded fluid is used.

The detector apparatus has, as already mentioned, not only the X-Y detector, but possibly also a Z detector, for which customary detector devices are used, for example, eddy current distance sensors. The X-Y detector determines the position of the integral rotor in the direction of the axis of rotation and emits a Z position signal, which is used for the technical control stabilization of the integral rotor in this direction. A magnetizing current, which can be set up in the drive direction with a current component in the flux direction, for instance, serves for this technical control stabilization. The mentioned Z position signal, or the control signal derived therefrom, also serves to determine the pump pressure with the help of a pressure determining device.

When the speed of rotation of the integral rotor and of the torque-forming component of the drive current are known, the amount of fluid forwarded per unit time can also be determined from the Z position signal.

Figure 17:
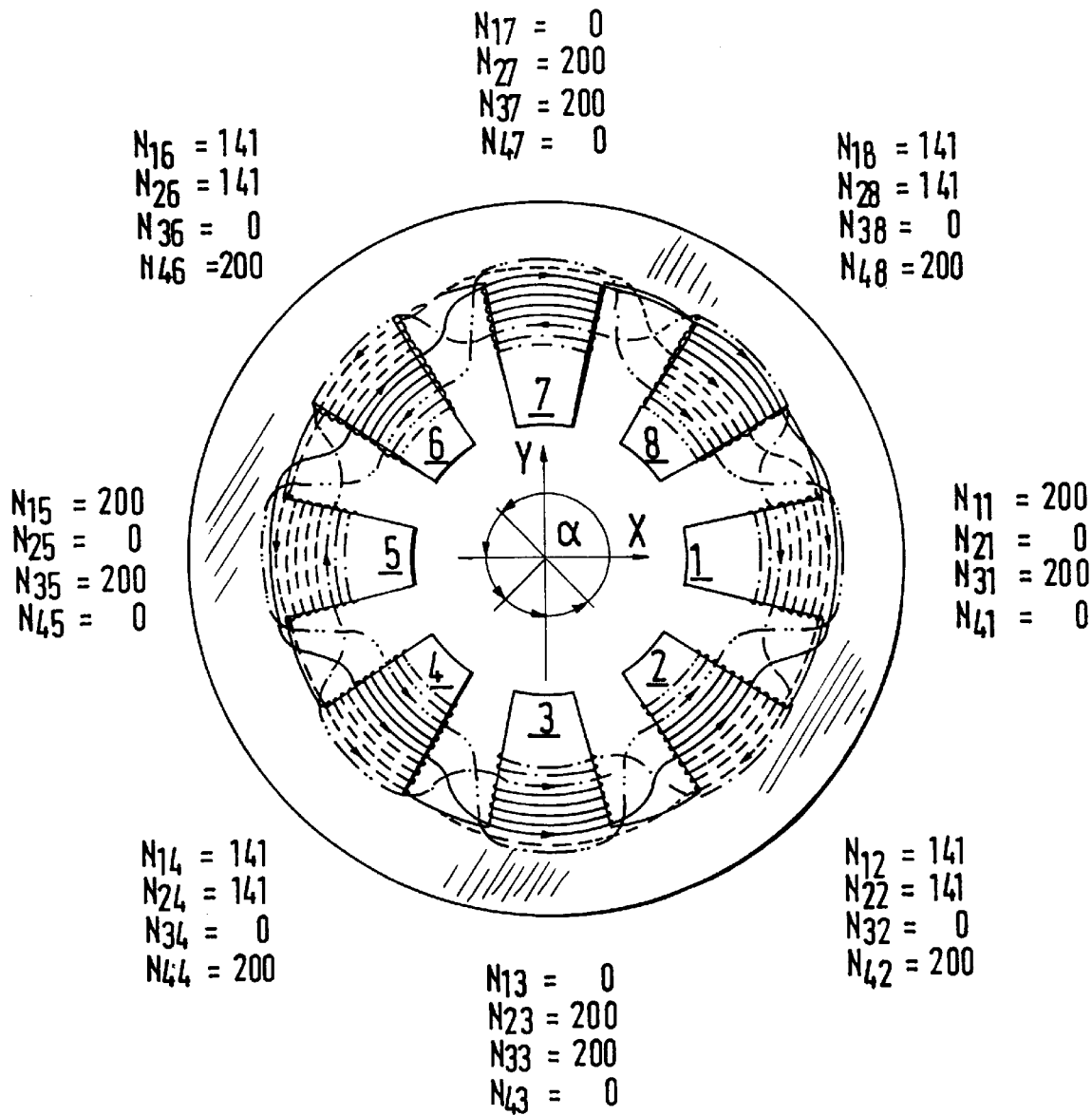
FIG. 17 is a stator in which the numbers of turns of the rotary field winding and the control winding are chosen in such a manner that a sinusoidal geometrical distribution of the drive-field flux and of the control-field flux are achieved.

FIG. 17 shows an example for the numbers of turns of the rotary field winding and the control winding, by means of which an at least approximately sinusoidal distribution of the drive flux and of the control flux is achieved. The number of turns depends on the cosine or the sine of the electrical angle of the position of the poles.

Figure 18:
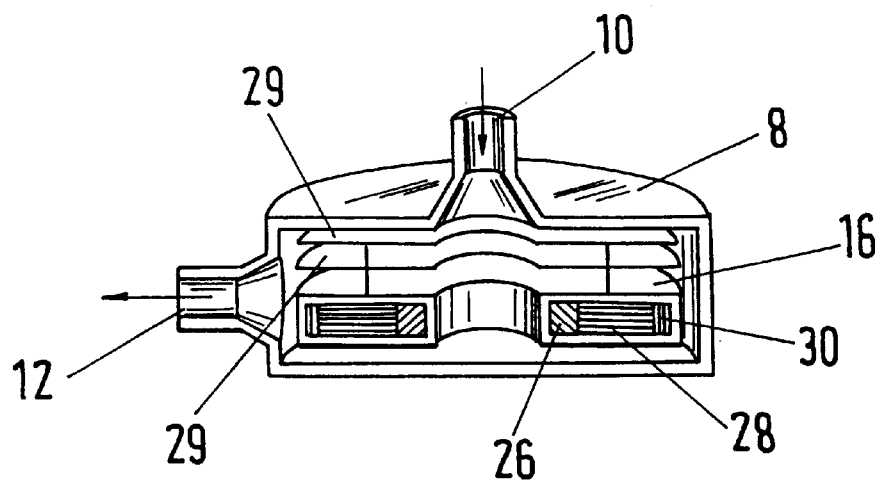
FIG. 18 is a Tesla pump with a driving rotor laterally integrated into the Tesla pump rotor to form an integral rotor.

In the Tesla pump shown in FIG. 18 the disc-shaped driving rotor consists of the rotor disc 16, the magnet 28, the yoke 26 and the conducting layer 30. This driving rotor 16 is assembled with the pump rotor plates 29 to form an integral Tesla pump rotor. The driving rotor is arranged laterally in the integral rotor and is built into the pump housing 8 with the inlet 10 and the outlet 12.

Figure 19:
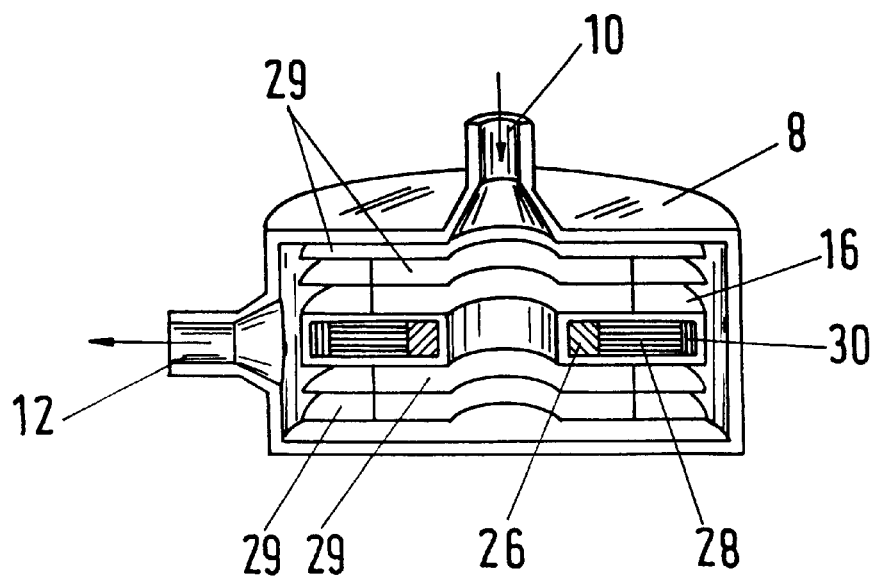
FIG. 19 is a Tesla pump with a driving rotor integrated into the interior of a Tesla pump rotor to form an integral rotor.

In contrast to the construction of FIG. 18, the driving rotor 16 in the integral rotor of the Tesla pump of FIG. 19 is installed between the pump rotor plates 29.

Figure 20:
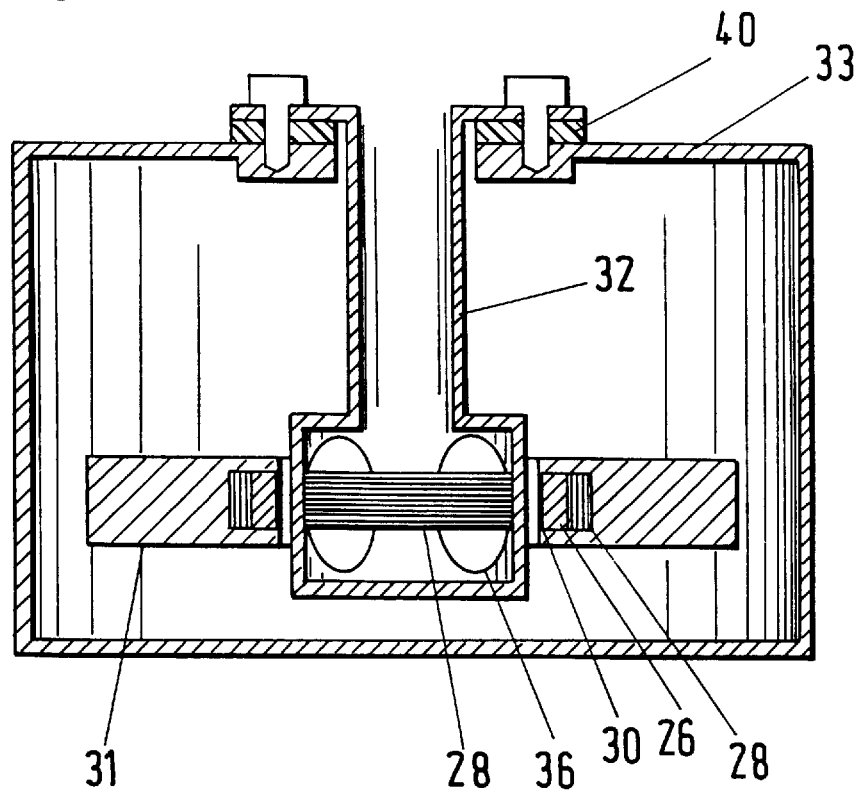
FIG. 20 is a split-tube stirring mechanism with a magnetically journalled integral stirring rotor in a split-tube.

In the split-tube stirring apparatus of FIG. 20 a stator with the yoke 38 and the windings 36 is built into the split-tube housing 32. The integral rotor 31 comprises the actual stirrer, into which the driving rotor with the magnet ring 28, the yoke 26 and a conducting layer 30 are integrated. The split-tube housing 32 is inserted in an opening in the stirring tank 33 and can be sealed with respect to the outer space by the seal 40. The matter to be stirred is located in the interior of the stirring tank 33.

Figure 21:
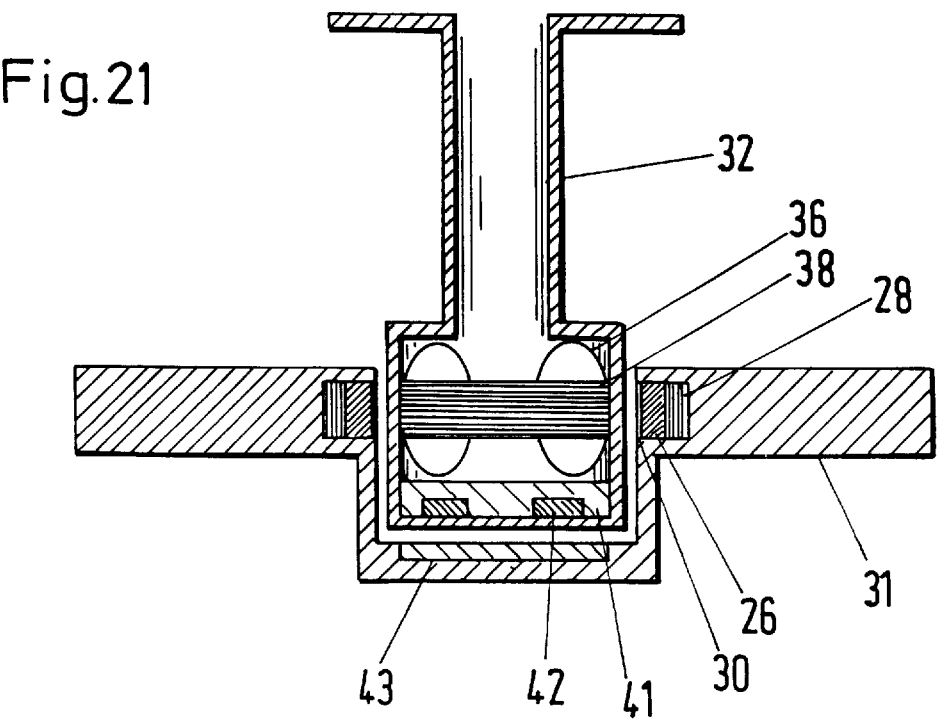
FIG. 21 is a split-tube stirring mechanism with a magnetically journalled integral stirring rotor in a split tube with an electromagnetic axial bearing for the integral rotor.

In the split-tube stirring apparatus of FIG. 21 an electromagnetic axial bearing with the stator 41 and with a stator winding 43 is additionally built into the split tube 32. The yoke iron 43 of the axial magnetic bearing with the stator 41 is likewise integrated into the stirrer 31.

The advantage of a bearing/drive arrangement in accordance with the principle of the reluctance motor (FIG. 8) or induction motor, in comparison with a synchronous motor excited by permanent magnets, lies in the fact that the integral rotor contains no expensive materials. This is of importance if the integral rotor belongs to a disposable part such as, for example, in a one-way blood pump. Disadvantageous both in a reluctance motor as well as in a synchronous motor is that the entire flux for the excitation of the drive field must be set up via a magnetisation current component in the drive winding. For large air gaps, the air gap magnetization requires enormously large magnetization currents, which produce large losses in the drive winding. Thus, the air gap attainable in induction and reluctance motors is limited to a few mm. Very large motors are an exception.

Figure 22:
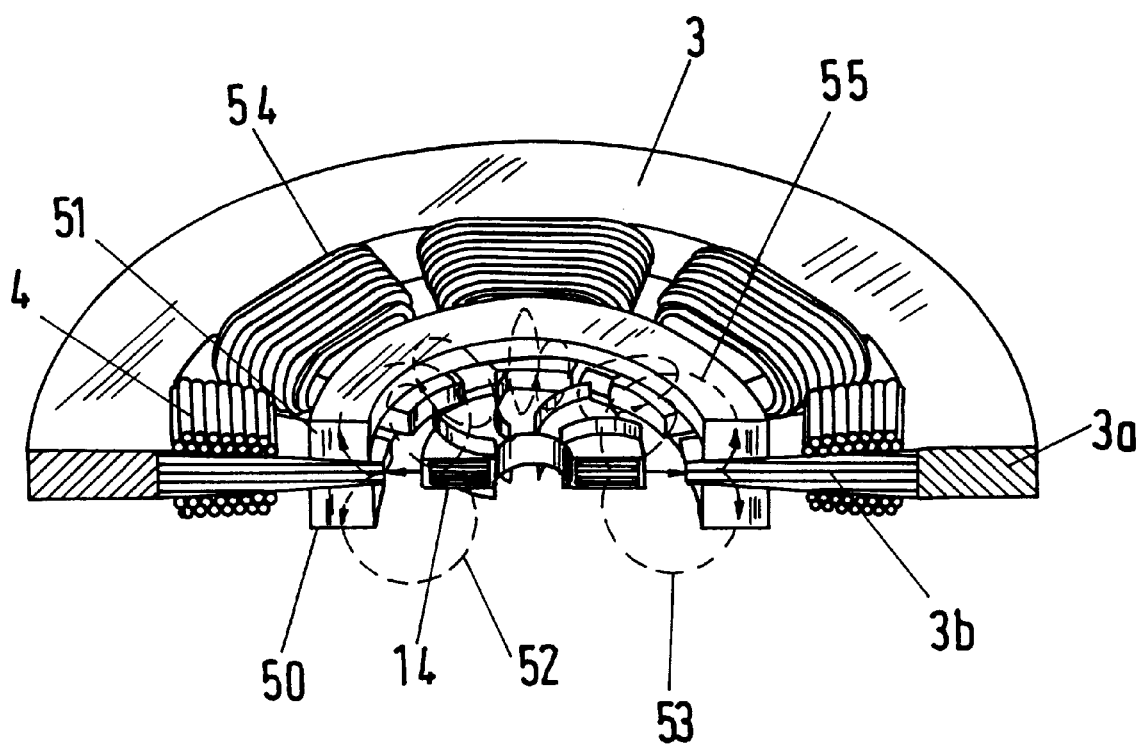
FIG. 22 is a further advantageous embodiment of a bearing/drive arrangement with permanent magnets in the stator.

A solution of this problem is found in that permanent magnets are arranged in the stator of the bearing/drive arrangement which produce a unipolar flux (this means that the flux, when considered over the entire periphery, passes either only from the stator to the rotor or only in the reverse direction). Together with a bipolar rotary field winding, forces can be produced on the integral rotor in the radial direction. With a further rotary field winding having a number of pole pairs p>2, a rotating rotary field component can be produced in addition which is suitable for driving the integral rotor, which is executed as a short-circuit rotor or as a rotor of a reluctance motor, and leads to no disturbing radial forces, either in cooperation with the unipolar flux or with the bipolar flux component. An advantageous embodiment of a rotary machine of this kind is shown in FIG. 22, which shows the stator 3 and the integral rotor 14 of the bearing/drive arrangement. The unipolar flux, represented by the unipolar flux lines 52, 53, 54, 55 as well as by further unipolar flux lines which are not named, is here excited by two laterally magnetized permanent magnets 50, 51 which are ring-shaped and arranged on both sides of the stator. Naturally, a plurality of small individual magnets can be used in place of the permanently magnetized rings. Furthermore, the magnets can also be arranged outside the winding. The bilateral arrangement of magnets is advantageous because the stray field lines which penetrate into the rotor are thereby symmetrical and therefore produce no axial pulling forces. The stator winding (4) thus contains both windings of a bipolar rotary field winding as well as a rotary field winding of higher polarity, preferably with the number of pole pairs equal to 3.

The rotary machine with a driven rotor and with an electric rotor comprises a stator and a driving rotor. The stator is executed as an electromagnetic bearing for the driving rotor, and the driving rotor of the electric motor together with the driven rotor of the rotary machine forms a rotor unit, i.e. an integral rotor.

This rotary machine comprises a rotary field winding with the number of pole pairs p for producing a driving rotary field and for the controlled rotation of the driving rotor about its axis of rotation as well as a control winding with the number of pole pairs p+1 or p+1 for producing a control field super imposed on the driving rotary field in order to regulate the radial position (two degrees of freedom) of the driven rotor in its plane of rotation, i.e. to actively stabilize it.

In the rotary machine the driving part of the integral rotor can be designed in disc shape, in ring shape or in bell shape and the rotor can be stabilized passively through reluctance forces both axially as well as against tilting with respect to the stator plane.

The rotary machine can have a rotor geometry which is such that at least one of the degrees of freedom of the rotor which is not actively stabilized is passively stabilized through hydrostatic or hydrodynamic forces, through aerostatic or aerodynamic forces or through gravitational forces.

In a rotary machine of this kind the stator, together with the driving rotor, can form a synchronous motor excited by permanent magnets or a reluctance motor, or the stator can form an external-rotor motor together with the driving rotor.

The permanent magnetic driving rotor can be executed as a ring magnet, a disc magnet or as shell magnets and can also constitute the rotor yoke or the iron cross part of the integral rotor.

In a rotary machine of this kind, the integral rotor can be constructed together with a part of the working apparatus as a unit which can be lifted off from the drive stator.

The drive stator of the rotary machine can be formed of individual, rod-like coils which are arranged radially about the rotor with a common magnetic yoke, and each of the coils can have one partial winding each for every winding string of the drive winding and of the control winding.

In the rotary machine the number of turns in the partial windings can be chosen in such a manner that the drive flux and the control flux are geometrically at least approximately sinusoidal.

For a two-phase bearing/drive unit the number of turns in each partial winding of the first phase (of both the drive winding and the control winding) can, for example, be a given number of turns $N_1$ times the cosine of the electric angle of its position alpha ($[N_1 \cos(p\, alpha)]$ for the drive winding and $[N_1 \cos\{(p\pm 1)\, alpha\}]$ for the control winding)

and the number of turns of each partial winding of the second phase (again of both the drive winding and the control winding) can be a given number of turns $N_2$ times the sine of the electric angle of its position alpha ($[N_2 \sin(p\ alpha)]$ for the drive winding and $[N_2 \sin\{(p\pm 1)alpha\}]$ for the control winding).

The drive stator of the rotary machine can be formed, with respect to the rotor in the axial direction, of coils arranged in the manner of a temple pillar, as a temple motor with a common magnetic yoke, with the flux at one coil end, on the side lying opposite the magnetic yoke, being conducted to the rotor through an L-shaped extension of the coil core oriented towards the rotor and with the coils having partial windings for each winding string of the drive winding and the control winding, with individual partial windings possibly having zero as the number of turns and with the at least approximately sinusoidal geometric distribution of the drive flux and the control flux being formed through the winding turn ratio between the individual partial coils.

In the rotary machine, flux sensors can be arranged in the air gap between the stator and rotor and/or in the coil cores in order to determine one or more partial flux components which are transferred to the drive and position control systems of the bearing-less motor by means for transmitting the measured partial flux components.

In the rotary machine the rotor position can be determined through a weighted summation of the partial fluxes over half the perimeter respectively in the x direction and y direction of the plane of rotation of the driving rotor and in the opposite direction, by taking the absolute value and by subsequently forming the difference of the component in the x direction and in the opposite direction as well as the component in the y direction and in the opposite direction. The angle and/or the magnitude of the drive flux angle can be determined from the partial fluxes.

In the rotary machine eddy current distance sensors can be arranged in the individual grooves or between individual coil cores of the drive stator which measure the distance from a conductive layer in the driving rotor in the plane of the rotor (X-Y plane).

Eddy current distance sensors of this kind can consist of a metallic ring or a thin metallic layer or of the conductive magnetic material of the driving rotor magnet.

In the x direction, and the y direction two oppositely disposed distance sensors can be employed in each case and the components of the position of the driving rotor in the plane of the rotor (x-y plane) can be determined from the difference of the sensor signals from oppositely disposed sensors. The drive stator of the rotary machine can have sensor windings in addition to the drive and control windings.

The axial position of the driving and the driven rotor of the rotary machine, i.e. of the integral rotor, can be stabilized in a regulated manner by a magnetization current in an additional axial coil.

A split tube can be arranged in a rotary machine between the drive stator and the integral rotor of the rotary machine.

The working apparatus driven by the rotary machine can, for example, be a rotary pump, in particular a medical pump for pumping blood, a stirring apparatus, a turbo machine, a spindle, a centrifuge or a galette. The rotary pump can, for example, be an axial pump, a centrifugal pump, a regenerative pump, a peripheral pump or a Tesla pump. The rotary machine executed as a rotary pump can have a closed pump housing which contains the integral rotor and encloses the driving rotor of the motor and the driven rotor of the pump.

The pump housing can advantageously be mounted on the drive stator so as to be freely accessible and replaceable from at least one side.

A rotary machine of this kind executed as an axial pump can have a ring-shaped driving rotor which surrounds the vaned wheel of the axial pump in a ring-like manner (hollow shaft rotor).

In a rotary machine of this kind executed as an axial pump, the pump housing can have an inlet stub at one side and an outlet stub at the other side. The pump can be inserted into the transport circuit via these stubs, and indeed advantageously in such a manner that the pump housing can be removed with the pump rotor from the driving stator after the removal of the preferably hose-like connections.

The rotary machine can also be executed as a centrifugal pump whose ring-shaped or disc-shaped driving rotor is integrated into a vaned wheel, preferably of plastic, or built onto the vaned wheel.

In a rotary machine executed as a rotary pump, the axial rotor position signal or the control signal of the control system which is used for the axial stabilization of the rotor can also be used to determine the pump pressure.

In a rotary machine executed as a rotary pump, means can be provided for determining the through-flow of fluid through the pump from the axial rotor position signal, from the speed of rotation of the rotor as well as from the torque-forming components of the drive current (Q-components).

In a rotary machine executed as a centrifugal pump, the pump housing can have an inlet and two outlets on both axial sides.

In a rotary machine in accordance with the invention, the axial length of the driving rotor can advantageously be less than or equal to half the diameter of this rotor.

The invention relates to a rotary pump for fluids with a hermetically sealed pump housing having at least one inlet and at least one outlet for the fluid and having a pump rotor which is suspended by a magnetic bearing apparatus and can be driven by a contact-free electrical drive device, with the magnetic bearing and the contact-free electrical drive device forming a bearing-less rotary field motor with a common bearing/drive rotor which is executed together with the pump rotor as an integral rotor 14, with the bearing-free rotary field motor having a drive winding with a number of pole pairs p and a control winding with a number of pole pairs p+1 or p−1, in such a manner that the rotation of the integral rotor 14 about its axis of rotation 3 can be actively controlled by means of the drive winding and the position of the integral rotor 14 in the plane (X-Y) extending perpendicular to the axis of rotation 3 can be actively controlled by means of the control winding, and in such a manner that the position of the integral rotor 14 along the axis of rotation Z and its tilting out of the named plane X,Y are passively stabilized through reluctance forces. The rotary pump can have a pump housing 8 in which the integral rotor 14 which is accommodated therein is arranged so as to be freely accessible and removable from the outside.

The integral rotor 14 of the rotary pump can have a ring-like rotor disc 16 in which the electromagnetically active components 26, 28, 30 are contained and on which the rotor blades 18, 19 are mounted. The pump rotor and the electromagnetically active components 26, 28, 30 can also be embedded in parts of the rotor disc 16 which are welded to one another or can be sprayed on it. In the rotary pump the surfaces of the pump housing 8 and of the integral rotor 14 which come into contact with the forwarded fluid can consist of plastic.

The pump housing 8 can have a further axial inlet 11 which lies opposite to the first axial inlet 10. The pump housing 8 can also have a further, at least approximately radial, outlet 13 which is centrally symmetrically arranged with respect to the first radial outlet 12. The rotary pump can advantageously be executed as an axial pump (FIG. 9).

The rotor blades 18 can be executed as vanes of a vaned wheel 24 which is mounted in the central recess of the ring-like rotor disc 16.

The rotary pump can also be a centrifugal pump such as shown in FIG. 11. In the rotary pump the rotor blades 18 can be arranged at a surface of the rotor disc 16. The rotor blades 18, 19 can be arranged at both sides of the rotor disc 16.

The bearing/drive stator of the rotary field motor of the rotary pump can have a plurality of elongate coil cores 34 arranged about the integral rotor 14 with a common magnetic yoke, with each coil core 34 containing a partial winding of the winding string of the drive winding with the number of pole pairs p and a partial winding of the winding string of the control winding with the number of pole pairs p+1 or p−1, with a sinusoidal geometric distribution of the drive flux and of the control flux being approximated by the ratios of the numbers of turns in the partial windings of a winding string, where one of the partial windings can have zero as the number of turns.

The coil cores 34 of the rotary pump can be arranged radially to the axis of rotation 3 of the integral rotor 14 and the coil cores 34 and the yoke iron can form a unit, with this unit being stacked up from individual lamina with long grooves. The coil cores 34 can have the shape of an L, one of whose limbs 35*a* are oriented parallel to the axis of rotation 3 of the integral rotor 14 and whose other limbs 35*b* are directed radially inwardly towards the axis of rotation 3 of the integral rotor 14 in order to conduct the flux radially to the integral rotor 14.

The rotary field motor can also be a synchronous motor, with the latter being a reluctance motor or a synchronous motor excited by permanent magnets.

In a rotary pump, an apparatus can be provided in order to determine at least one partial flux component, through which the drive flux angle required for the drive regulation of the bearing-less motor can be determined. This apparatus can have at least one flux sensor 50*x*, 50*y*, 51*x*, 51*yn*, 50*a* to 50*h*. Furthermore, the rotary pump can have a detector device for determining the position of the integral rotor 14. This detector apparatus can have an X-Y detector in order to determine the position of the integral rotor (14) along the axes X and Y. The X-Y detector can have at least one flux sensor 50*x*, 50*y*, 51*x*, 51*y*, 50*a* to 50*h*.

A plurality of symmetrically distributed flux sensors 50*x*, 50*y*, 51*x*, 51*y*, 50*a* to 50*h* can be provided for the measurement of partial fluxes at discrete positions, and from the partial fluxes the X and Y components of the position of the integral rotor 14 can be determined, in addition to the rotational angle of the motor via the drive flux angle, by a weighted summation of the partial fluxes over half the periphery in each case in the positive and negative X and Y directions, by taking the absolute value and by subsequently forming the difference of the component in the positive and negative X direction as well as of the component in the positive and negative Y direction.

In a rotary pump of this kind, at least one flux sensor 50*x*, 50*y*, 51*x*, 51*y*, 50*a* to 50*h* can be arranged in the air gap between the pump housing 8 and the bearing/drive stator, wherein the at least one flux sensor 50*x*, 50*y*, 51*x*, 51*y*, 50*a* to 50*h* can be arranged in the coil core 34, 35. The at least one flux sensor could, however, also be a magnetorestrictive flux sensor.

The at least one flux sensor can be mounted on a tooth of the stator of the rotary field motor, for example glued on. The at least one flux sensor can be embedded in an extension of a tooth of the stator of the rotary field motor. The X-Y detector can contain at least one eddy current distance sensor in order to measure the distance from a conductive layer in the integral rotor in the X-Y plane.

The conductive layer 30 can consist of a metallic ring or a thin metallic layer or of the magnets 28 if the latter are constructed of a conducting material, for example NdFe.

In the rotary pump, two eddy current distance sensors lying opposite to one another can be provided in the X direction and in the Y direction in each case in order to win the components of the position of the integral rotor in the X-Y rotor plane from the difference of the sensor signals of the mutually oppositely disposed eddy current distance sensors.

The X-Y detector can contain sensor windings which are arranged in the stator of the rotary field motor, in addition to the drive and control windings, in order to determine the position of the integral rotor 14 by determining the electrical impedance of the sensor windings. The X-Y detector can also contain an optical device for measuring the position of the integral rotor by means of light whereby the wavelength lies in the optical range of the fluid. The detector device can also comprise a Z detector for determining the axial position of the integral rotor and for deriving a corresponding Z position signal.

The Z position signal can form the actual value for determining a control signal for a technical control stabilization of the axial position of the integral rotor. A magnetizing current can be set up in the drive winding with a current component in the flux direction for the technical control stabilization of the axial position of the integral rotor.

A pressure measuring device can also be provided in order to determine the pump pressure from the Z position signal or from the control signal determined therefrom.

In addition, a through-flow determining apparatus can be provided in order to determine the through-flow from the Z position signal and from the speed of rotation of the integral rotor and from the torque-forming components of the drive current.

In the electromagnetic rotary drive with a magnetically suspended rotor, for a working apparatus, the stator of the rotary drive is also executed as a magnetic bearing for the rotor and comprises a stator part with a drive winding for the production of a p-pole-paired rotary drive field for driving the rotor. Furthermore, the rotary drive comprises a bearing winding for the rotary drive and for the production of a (p+1)-pole-paired or (p−1)-pole-paired bearing field as well as a control system for regulating the bearing field in a plane, and thus for determining the position of the rotor in this plane transverse to its axis of rotation. The stator and the rotor are designed in such a manner that the rotor is stabilized in its position by restoring forces/reluctance forces.

In the electromagnetic rotary drive the stator can form a synchronous motor excited by permanent magnets or reluctance motor together with a part of the working apparatus to be driven.

The electromagnetic rotary drive can be designed 2p-pole-wise and the rotor can be executed as a magnet, for example as a ring, disc or shell magnet, with or without a yoke iron, or the iron cross can be designed as a part of a rotating part of the working apparatus.

In a rotary drive of this kind, the working apparatus to be driven can be formed together with the rotor as a unit which can be lifted off from the stator. In the electromagnetic rotary drive, the geometric distribution of the drive flux and of the bearing flux can be approximated with the help of winding ratios of the individual partial coils.

The stator can be built up of individual coils arranged radially about the rotor with a common magnetic yoke and the coil cores can each carry a winding of the drive winding and the control winding.

The stator can, in relation to the rotor in the axial direction, be built up of coils arranged in the manner of the pillar of a temple (temple motor) with a common magnetic yoke whose coil cores have an L-shaped part which lead radially to the rotor, with the coils which are arranged in the manner of the pillars of a temple having partial windings of the drive, and stator windings.

In the electromagnetic rotary drive, one or more sensors such as Hall elements or magnetorestrictive elements can be arranged in the air gap between the stator and the rotor for the determination of the magnetic flux or of magnetic partial fluxes or eddy current distance sensors can be provided, the measurement values of which are fed to the drive and position control system in order to determine and regulate the drive flux angle of the bearing-less motor.

The position of the rotor can also be determined in an electromagnetic rotary drive of this kind with the help of impedance measurements of sensor windings in the stator with ultrasonic echography or by optical means.

The axial position of the rotor of the rotary drive can be regulated and stabilized through setting up a magnetizing current in the drive winding or with an additional axial coil on the one side of the rotor.

The electromagnetic rotary drive is suitable as a drive for a radial pump, an axial pump, a centrifugal pump, a Tesla pump, or a mixing or stirring apparatus. In these arrangements, the pump rotor or the mixing or stirring rotor, as well as the rotor of the motor, can be enveloped in plastic.

If the electromagnetic rotary drive is used as the drive for a pump, the pump pressure can be determined from the axial rotor position signal or from the control signal required for the axial stabilization. Alternatively, the through-flow of the pump can be determined from the axial rotor position signal from the speed of rotation of the rotor as well as from the torque-forming components of the driving current (Q-components).

Electromagnetic rotary drives of the kind described are suitable as a drive for a rotary pump for pumping blood. Blood pumps of this kind are used, for example, in medical operations.

In an electromagnetic rotary drive in accordance with the invention, the axial position of the driving rotor is advantageously smaller than or equal to half the diameter of this rotor.

An electromagnetic rotary drive in accordance with the invention can also be executed in a miniaturized version, for example, as a blood pump which can be implanted in an animal or a person.

The rotary machine comprises a driven rotor 2 and an electric motor 4, 14 having a stator 4 and a driving rotor 14. The stator 4 is also executed as an electromagnetic bearing 4, 14 for the driving rotor 14, and the driving rotor 14 of the electric motor 4, 14 together with the driven rotor 2 of the rotary machine forms a rotor unit 2, 14, i.e. the two rotors 2, 14 form an integral rotor 2, 14. The rotary machine can, for example, be a rotary pump, a centrifugal pump, a centrifuge or a stirring apparatus. The rotor 2, 14 can be constructed so as to be easily removable from the stator 4.

What is claimed is:

1. A rotary machine comprising a driven rotor and an electric motor that includes only a single stator and a driving rotor; wherein the stator is also executed as an electromagnetic bearing for the driving motor and includes a portion that effects magnetic suspension of the rotor and effects driving of the rotor; wherein the driving rotor of the electric motor together with the driven rotor of the rotary machine forms a rotary unit.

2. A rotary machine in accordance with claim 1 in which the driving part of the rotor unit is designed to be one of disc-shaped, ring-shaped, or bell-shaped; and in that the rotor is passively stabilized by reluctance forces both axially as well as against tilting with respect to plane of the stator.

3. A rotary machine in accordance with claim 1 in which the stator together with the driving rotor forms an external rotor motor.

4. A rotary machine in accordance with claim 1 in which the rotor unit is constructed together with a part of the rotor machine as a unit which can be lifted off from the drive stator.

5. A rotary machine in accordance with claim 1 in which the drive stator is built up of individual, rod-shaped coils arranged radially about the rotor with a common magnetic yoke and each coil has partial windings for each winding string of the drive winding and of the control winding.

6. A rotary machine in accordance with claim 1 in which the drive stator is executed, with respect to the rotor in the axial direction, of coils arranged in the manner of the pillars of a temple as a temple motor having a common magnetic yoke, with the flux at one coil end, at the side lying opposite the magnetic yoke, being conducted radially to the rotor through an L-shaped extension of the coil core pointing towards the rotor, and with the coils having partial windings for each winding string of the drive winding and the control winding, where individual partial windings can have 0 as the number of turns and the at least approximately sinusoidal geometrical distribution of the drive flux and the control flux is formed by the winding turn ratio between the individual partial coils.

7. A rotary machine in accordance with claim 1 in which eddy current distance sensors are arranged in individual grooves or between individual coil cores of the drive stator and measure the distance to a conducting layer in the driving rotor in a rotor plane.

8. A rotary machine in accordance with claim 1 in which two oppositely disposed distance sensors are used in the X direction and the Y direction in each case and the components of the position of the driving rotor in a rotor plane are determined from the difference of the sensor signals of oppositely disposed sensors.

9. A rotary machine in accordance with claim 1 in which sensor windings are arranged in the drive stator in addition to the drive and control windings.

10. A rotary machine in accordance with claim 1 in which an axial position of the rotor is regulated and stabilized through the application of a magnetization current in the drive winding or by means of an additional axial coil at the one side of the rotor.

11. A rotary machine in accordance with claim 1 in which a split tube is arranged between the drive stator and the integral rotor.

12. A rotary machine in accordance with claim 1, executed as a rotary pump, with a closed pump housing which contains an rotor unit which encloses the driving rotor of the motor and the driven rotor of the pump.

13. A rotary machine in accordance with claim 1, executed as a rotary pump, with a pump housing that is arranged on the drive stator in such a manner as to be freely accessible and replaceable from at least one side.

14. A rotary machine in accordance with claim 1, executed as an axial pump, with a ring-shaped driving rotor which surrounds the vaned wheel of the axial pump in a ring-like manner.

15. A rotary machine executed as an axial pump in accordance with claim 1, the pump housing of which has an inlet stub at the one side and an outlet stub at the other side via which stubs the pump is inserted into the forwarding circuit in such a manner that the pump housing can be removed with the pump wheel from the driving stator after removal of the preferably hose-like connections.

16. A rotary machine in accordance with claim 1, executed as a centrifugal pump, whose ring-shaped or disc-shaped driving rotor is integrated into a vaned wheel or is mounted onto the vaned wheel.

17. A rotary machine in accordance with claim 1, executed as a rotary pump, in which the axial rotor position signal or the control signal of the control system which is required for the axial stabilization of the rotor is used for the determination of the pump pressure.

18. A rotary machine, executed as a rotary pump, in accordance with claim 1 with means for determining the through-flow of a fluid through the pump from the axial rotor position signal from the speed of rotation of the rotor and from the driving current.

19. A rotary machine in accordance with claim 1 in which the axial length of the driving rotor is smaller than or equal to half the diameter of this rotor.

20. A rotary machine in accordance with claim 1 wherein means are present in the stator which produce a unipolar flux in the electric motor; and wherein the stator has a bipolar rotary field winding via which radial magnetic fields acting on the rotor can be controlled; and wherein the stator has a further rotary field winding with a number of pole pairs p, $p \geq 2$, via which a rotary field can be produced for driving the rotor.

21. A rotary machine in accordance with claim 20 wherein the unipolar flux in the electric motor is produced by permanent magnets.

22. A rotary machine in accordance with claim 1 comprising
   a rotary winding with a number of pole pairs p for the production of a rotary driving field and for the controlled rotation of the driving rotor about its axis of rotation, and
   a control winding with a number of pole pairs p+1 or p−1 for the production of a control field superimposed on the rotary driving field in order to regulate a radial position of the driven rotor in its plane of rotation in a controlled manner.

23. A rotary machine in accordance with claim 22 in which a number of turns of the partial windings is chosen in such a manner that a drive flux and a control flux are geometrically at least approximately sinusoidal.

24. A rotary machine in accordance with claim 23 with a two phase winding in which the number of turns of each partial winding of the first phase is a given number of turns $N_1$ or $N_1$, respectively, times the cosine of the electric angle alpha of its position ([$N_1$ x cos (p alpha)] for the drive winding and [$N_1$ x cos {(p±1 alpha}] for the control winding) and the number of turns of each partial winding of the second phase is a given number of turns $N_1$ and $N_2$, respectively, times the sine of the electric angle alpha of its position ([$N_2$ x sin (p alpha)] for the drive winding and [$N_2$ x sin {(p±1 alpha}] for th conrol winding) or vice versa.

25. A replaceable unit comprising:
   a housing having an inlet for a fluid to be forwarded from the inlet through the housing to the outlet; and
   a driving rotor and a driven rotor arranged within the housing, the driving rotor and thge driven rotor forming an integral rotor, which is adapted to be magnetically suspended and driven by the poles of only a single stator and includes a portion that effects magnetic syspension of the rotor and effects driving of the rotor, the integral rotor having means thereon for forwarding the fluid the inlet to the outlet upon rotation of the integral rotor.

26. A replaceable unit in accordance with claim 25, wherein the housing is made from plastics and forms a disposable unit with the integral rotor.

27. A replaceable unit in accordance with claim 26, wherein the integral rotor has a ring-shaped rotor disc in which electromagnetically active components of the integral rotor are accommodated and to which rotor blades are fastened.

28. A replaceable unit in accordance with claim 27, wherein the electromagnetically active components of the integral rotor comprise permanent magnets as well as iron.

29. A replaceable unit in accordance with claim 25, wherein the integral rotor has a ring-shaped rotor disc in which electromagnetically active components of the integral rotor are accommodated and to which rotor blades are fastened.

* * * * *